US010779533B2

(12) United States Patent
Pettigrew et al.

(10) Patent No.: US 10,779,533 B2
(45) Date of Patent: *Sep. 22, 2020

(54) CLEANSING COMPOSITION HAVING A PRESERVATIVE SYSTEM AND A WET WIPE COMPRISING THE CLEAN COMPOSITIONS

(71) Applicant: The Procter & Gamble Company, Cincinnati, OH (US)

(72) Inventors: Charles Allen Pettigrew, West Chester, OH (US); Justin Angelo Caserta, Mason, OH (US); Donna Jane Wiedemann, West Harrison, IN (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/718,805

(22) Filed: Dec. 18, 2019

(65) Prior Publication Data

US 2020/0120928 A1 Apr. 23, 2020

Related U.S. Application Data

(63) Continuation of application No. 14/330,171, filed on Jul. 14, 2014, now Pat. No. 10,542,750.

(60) Provisional application No. 61/846,102, filed on Jul. 15, 2013.

(51) Int. Cl.

| | |
|---|---|
| A01N 37/10 | (2006.01) |
| A01N 25/34 | (2006.01) |
| A61K 8/37 | (2006.01) |
| A61K 8/02 | (2006.01) |
| A01N 37/36 | (2006.01) |
| A61K 8/34 | (2006.01) |
| A61K 8/36 | (2006.01) |
| A61K 8/365 | (2006.01) |
| A61K 8/362 | (2006.01) |
| A61Q 19/10 | (2006.01) |
| A61K 8/368 | (2006.01) |

(52) U.S. Cl.
CPC ............ *A01N 37/10* (2013.01); *A01N 37/36* (2013.01); *A61K 8/0208* (2013.01); *A61K 8/345* (2013.01); *A61K 8/36* (2013.01); *A61K 8/362* (2013.01); *A61K 8/365* (2013.01); *A61K 8/368* (2013.01); *A61K 8/375* (2013.01); *A61Q 19/10* (2013.01); *A61K 2800/524* (2013.01)

(58) Field of Classification Search
CPC ...... A61K 8/0208; A01N 25/30; A01N 25/34; A01N 37/10

See application file for complete search history.

(56) References Cited

U.S. PATENT DOCUMENTS

| | | |
|---|---|---|
| 3,967,756 A | 7/1976 | Barish |
| 3,982,659 A | 9/1976 | Ross |
| 3,986,479 A | 10/1976 | Bonk |
| 3,994,417 A | 11/1976 | Boedecker |
| 4,323,468 A | 4/1982 | Grollier et al. |
| 4,471,881 A | 9/1984 | Foster |
| 4,840,270 A | 6/1989 | Caputo et al. |
| 4,971,220 A | 11/1990 | Kaufman et al. |
| 5,050,737 A | 9/1991 | Joslyn et al. |
| 5,143,679 A | 9/1992 | Weber et al. |
| 5,322,178 A | 6/1994 | Foos |
| 5,366,104 A | 11/1994 | Armstrong |
| 5,518,801 A | 5/1996 | Chappell et al. |
| 5,525,588 A | 6/1996 | Michetti |
| 5,628,097 A | 5/1997 | Curro et al. |
| 5,647,506 A | 7/1997 | Julius |
| 5,658,639 A | 8/1997 | Curro et al. |
| 5,785,179 A | 7/1998 | Buczwinski et al. |
| 5,791,465 A | 8/1998 | Niki et al. |
| 5,914,084 A | 6/1999 | Benson et al. |
| 5,916,661 A | 6/1999 | Curro et al. |

(Continued)

FOREIGN PATENT DOCUMENTS

| | | |
|---|---|---|
| EP | 2243462 | 10/2010 |
| JP | H0267247 | 3/1990 |

(Continued)

OTHER PUBLICATIONS

Pilz, Dr. Frederic, "Sorbitan Caprylate—the Preservative Boosting, Multifunctional Ingredient", Cosmetic Science Technology, 2011, p. 131.

(Continued)

*Primary Examiner* — Lakshmi S Channavajjala

(74) *Attorney, Agent, or Firm* — Daniel S. Albrecht; Christian M. Best

(57) ABSTRACT

A wet wipe includes a cleansing composition and a substrate. The cleansing composition includes a preservative enhancing agent selected from the group consisting of caprylyl glycol; caprylyl glyceryl ether; glyceryl caprylate; sorbitan caprylate; ethylhyexyl glycerin, and combinations thereof. The cleansing composition includes a preservative selected from the group consisting of benzoic acid; lactic acid; sorbic acid; malic acid; maleic acid, and combinations thereof. The cleansing composition has a pH less than about 4. A method of making the cleansing composition may include dissolving one or more preservatives with water to form a solution; adding a rheology modifier to the solution; adding an emulsifier to the solution; adding a preservative enhancing agent to the solution; and adding citric acid to the solution.

20 Claims, No Drawings

(56) References Cited

U.S. PATENT DOCUMENTS

| | | |
|---|---|---|
| D414,637 S | 10/1999 | Amundson et al. |
| D416,794 S | 11/1999 | Cormack |
| D421,901 S | 3/2000 | Hill |
| D421,902 S | 3/2000 | Hill |
| 6,092,690 A | 7/2000 | Bitowft et al. |
| 6,114,263 A | 9/2000 | Benson et al. |
| 6,129,801 A | 10/2000 | Benson et al. |
| D437,686 S | 2/2001 | Balzar et al. |
| D443,451 S | 6/2001 | Buck et al. |
| D443,508 S | 6/2001 | Braaten et al. |
| D445,329 S | 7/2001 | Zethoff |
| 6,269,969 B1 | 8/2001 | Huang et al. |
| 6,269,970 B1 | 8/2001 | Huang et al. |
| 6,296,144 B1 | 10/2001 | Tanaka et al. |
| 6,315,114 B1 | 11/2001 | Keck et al. |
| D451,279 S | 12/2001 | Chin |
| 6,383,431 B1 | 5/2002 | Benson et al. |
| 6,401,968 B1 | 6/2002 | Huang et al. |
| 6,412,634 B1 | 7/2002 | Flaig et al. |
| 6,440,437 B1 | 8/2002 | Krzysik |
| 7,005,557 B2 | 2/2006 | Klofta et al. |
| 7,037,569 B2 | 5/2006 | Curro et al. |
| 7,410,683 B2 | 8/2008 | Curro et al. |
| 7,553,532 B2 | 6/2009 | Turner et al. |
| 7,666,827 B2 | 2/2010 | Marsh et al. |
| 8,221,774 B2 | 7/2012 | Marsh et al. |
| 8,987,180 B2 | 3/2015 | Wenzel et al. |
| 2002/0064323 A1 | 5/2002 | Chin |
| 2004/0091446 A1 | 5/2004 | Massaro et al. |
| 2008/0311231 A1 | 12/2008 | Modak et al. |
| 2009/0263439 A1* | 10/2009 | Casas-Sanchez ...... A01N 37/10 424/411 |
| 2010/0158964 A1 | 6/2010 | Cunningham et al. |
| 2011/0104085 A1 | 5/2011 | Klug et al. |
| 2011/0159074 A1 | 6/2011 | Warren et al. |
| 2011/0244199 A1 | 10/2011 | Brennan et al. |
| 2011/0268777 A1 | 11/2011 | Marsh et al. |
| 2012/0066852 A1 | 3/2012 | Trinkhaus et al. |
| 2012/0101135 A1 | 4/2012 | Klug et al. |
| 2012/0245132 A1 | 9/2012 | Zeng et al. |
| 2013/0022562 A1 | 1/2013 | Maunsell et al. |
| 2013/0039961 A1 | 2/2013 | Gonzales |
| 2014/0349902 A1 | 11/2014 | Allef et al. |
| 2015/0017218 A1 | 1/2015 | Pettigrew et al. |
| 2016/0089314 A1 | 3/2016 | Marsh |

FOREIGN PATENT DOCUMENTS

| | | |
|---|---|---|
| JP | 2007320873 | 12/2007 |
| JP | 2008100991 | 5/2008 |
| WO | WO 9955213 | 11/1999 |
| WO | WO 0027268 | 5/2000 |
| WO | WO 0214172 | 2/2002 |
| WO | WO 2007070795 | 6/2007 |
| WO | WO 2008129494 | 10/2008 |

OTHER PUBLICATIONS

"Velson™ SC, Ingredient for the Cosmetic Industry" Clariant International Ltd., Division Functional Chemicals, Jun. 2010, 2 pages.

International Search Report, PCT/US2014/046473, dated Nov. 14, 2014, 12 pages.

Kaß, et al., "Systemic Investigations in the Antimicrobial Efficacy of Glycerine Esters With Fatty Acids of Different Chain Length", Inform, Jun. 2014, vol. 25 (6), pp. 390-393.

All Office Action, U.S. Appl. No. 14/867,059.

All Office Action, U.S. Appl. No. 14/330,171.

International Search Report and Written Opinion, PCT/US2014/046473, dated Nov. 14, 2014, 12 pages.

* cited by examiner

CLEANSING COMPOSITION HAVING A PRESERVATIVE SYSTEM AND A WET WIPE COMPRISING THE CLEAN COMPOSITIONS

CROSS REFERENCE TO RELATED APPLICATIONS

This application is a continuation of, and claims priority under 35 U.S.C. § 120 to, U.S. patent application Ser. No. 14/330,171, filed on Jul. 14, 2014, which claims the benefit, under 35 U.S.C. § 119(e), of U.S. Provisional Patent Application Ser. No. 61/846,102, filed on Jul. 15, 2013, both of which are fully incorporated by reference herein.

FIELD

The present disclosure includes a cleansing composition for use in a wet wipe. The cleansing composition comprises a preservative system for limiting the growth of microbes.

BACKGROUND

Wet wipes are constructed from porous or absorbent sheets impregnated with a lotion and they are sold and stored in an air-tight container or wrapper to prevent the sheets drying out. Wet wipes are made for a variety of uses. The two main categories of use are firstly, those for general household cleaning tasks, such as the cleaning of hard surfaces like floors or kitchen surfaces and secondly those made for personal cleansing, such as the removal of make up, or the cleaning of infants prior to the fitting of a new diaper or the simple refreshment of the skin after meals or while traveling. Wipes have also found use with feminine health and adult incontinence products.

A major proportion of the wipes intended for the cleansing of human skin are wet wipes which are designed for the use with infants and young children. They are particularly used by parents during the changing of babies to clear away any excess fecal or urine residues in the peri-anal region before applying a fresh diaper or nappy. Wet wipes are required to be effective cleaning agents while at the same time being very gentle and mild on the skin of the baby. This is especially important given that the skin of the baby around the genitals and anus can become very sensitive after extended contact with urine and fecal matter.

The dual aim of providing effective cleaning while at the same time being mild on the skin is usually a balancing act for the manufactures of wet wipes. This is because the chemical compounds required for effective cleaning and preservation of the wet wipe are often those that are the least mild on human skin.

For regulatory approval for wet wipe products there are strict limits to the growth of microbes within the lotion/substrate media that are allowed. To reach these standards all wipe products to date have required some degree of preservation, from known preservative compounds.

It would be desirable to develop a mild wet wipe that has antimicrobial activity and providing an alternative to known preservative compounds.

SUMMARY

Aspects of the present disclosure may include a wet wipe comprising a cleansing composition and a substrate, wherein the cleansing composition comprises: a preservative enhancing agent selected from the group consisting of caprylyl glycol; caprylyl glyceryl ether; glyceryl caprylate; sorbitan caprylate; ethylhyexyl glycerin, and combinations thereof; a preservative selected from the group consisting of benzoic acid; lactic acid; sorbic acid; malic acid; maleic acid, and combinations thereof,
wherein the cleansing composition has a pH less than about 4.

Aspects of the present disclosure include a method of making a cleansing composition, the method comprising the steps of: dissolving one or more preservatives with water to form a solution;
adding a rheology modifier to the solution; adding an emulsifier to the solution; adding a preservative enhancing agent to the solution; and adding citric acid to the solution.

The rheology modifier may comprise xanthan gum. The preservative enhancing agent may comprise sorbitan caprylate. The preservative may comprise sodium benzoate. The preservative enhancing agent may be selected from the group consisting of caprylyl glycol; caprylyl glyceryl ether; glyceryl caprylate; sorbitan caprylate; ethylhyexyl glycerin, and combinations thereof. The preservative may be selected from the group consisting of benzoic acid; lactic acid; sorbic acid; malic acid; maleic acid, and combinations thereof. The cleansing composition may have a pH of less than about 4.

The step of adding a rheology modifier to the solution may occur subsequent to the step of dissolving one or more preservatives with water to form a solution. The step of adding an emulsifier to the solution may occur subsequent to the step of adding a rheology modifier to the solution. The step of adding a preservative enhancing agent to the solution may occur subsequent to the step of adding emulsifiers to the solution. The step of adding citric acid to the solution may occur subsequent to the step of adding a preservative enhancing agent to the solution.

Aspects of the present disclosure include a method of making a cleansing composition, the method comprising the steps of: mixing water with disodium ethylenediamine tetraacetic acid, sodium benzoate, and trisodium citrate to form a dispersion; adding xanthan gum to the dispersion; adding Peg-40 hydrogenated castor oil to the dispersion; adding BIS-PEG/PPG-16/16 PEG/PPG-16/16 dimethicone caprylic capric triglyceride to the dispersion; and adding a preservative enhancing agent to the dispersion.

The preservative enhancing agent may be selected from the group consisting of caprylyl glycol; caprylyl glyceryl ether; glyceryl caprylate; sorbitan caprylate; ethylhyexyl glycerin, and combinations thereof. The cleansing composition may have a pH of less than about 4.

DETAILED DESCRIPTION

The following definitions may be useful in understanding the present disclosure:

"Soil" refers herein to matter that is extraneous to a surface being cleaned. For example, soils include body exudates, household matter, and outdoor matter. Body exudates include feces, menses, urine, vomitus, mucus, and the like. Household matter includes food, beverages, combinations thereof, and the like. Outdoor matter includes dirt, mud, snow, paint, crayons, and the like.

"Substrate" refers herein to a material which is primarily two-dimensional (i.e. in an XY plane) and whose thickness (in a Z direction) is relatively small (i.e. 1/10 or less) in comparison to the substrate's length (in an X direction) and width (in a Y direction). Non-limiting examples of substrates include a web, layer or layers or fibrous materials, nonwovens, films and foils such as polymeric films or metallic foils. These materials may be used alone or may comprise two or more layers joined together. As such, a web is a substrate.

"Nonwoven" refers herein to a fibrous structure made from an assembly of continuous fibers, coextruded fibers, non-continuous fibers and combinations thereof, without weaving or knitting, by processes such as spunbonding, carding, meltblowing, airlaying, wetlaying, coforming, or other such processes known in the art for such purposes.

"Loading" refers to a process of applying a cleansing composition to a substrate to form a wet wipe. A "loaded" substrate is associated with a cleansing composition.

"Q.S." refers herein to "quantum sufficit" and is a sufficient percentage of water added to the composition to bring the overall composition to 100%.

As used herein, percentages are given as the weight of the component to the total weight of the cleansing composition, unless otherwise indicated. Percentages reflect 100% active component material. For example, if a component is available in a dispersion at a concentration of 50% component to dispersion, by weight, twice as much of the dispersion, by weight, would be added to the cleansing composition to provide the equivalent of 100% active component.

Values disclosed herein as ends of ranges are not to be understood as being strictly limited to the exact numerical values recited. Instead, unless otherwise specified, each numerical range is intended to mean both the recited values and any integers within the range. For example a range disclosed as "1 to 10" is intended to mean "1, 2, 3, 4, 5, 6, 7, 8, 9, 10."

While the present disclosure references the use of a wet wipe for cleaning skin, it is to be appreciated that the cleansing composition of the present disclosure may be used with various substrates, including tissues, paper towel, toilet paper, and the like. The substrates may be directly loaded with a cleansing composition or a cleansing composition may be applied to the substrate at the time of use in the form of a liquid or spray. In addition, the substrates of the present disclosure may be used to clean various other surfaces other than skin, including countertops, walls, floors, and the like. Moreover, the cleansing compositions of the present disclosure may be used as laundry detergents, facial cleansers, and the like.

Cleansing Composition

Controlling microbiological growth may be beneficial in water based products such as cleansing compositions intended for use in wet wipes. The cleansing composition may comprise a preservative system. In some exemplary configurations, the preservative system may include a preservative enhancing agent and one or more preservatives. A preservative may be understood to be a chemical or natural compound or a combination of compounds reducing the growth of microorganisms, thus enabling a longer shelf life for a package of substrates (opened or not opened) as well as creating an environment with reduced growth of microorganisms when transferred to the skin during the wiping process.

The spectrum of activity of the preservative may include bacteria, molds and yeast. Each of such microorganisms may be killed by the preservative. Another mode of action to be contemplated may be the reduction of the growth rate of the microorganisms without active killing. Both actions however result in a drastic reduction of the population of microorganisms.

Low pH buffering systems, such as a citrate-citric acid buffering system at a pH of less than about 5, may also be employed as part of the preservative system. In some exemplary configurations, acidic compounds used in sufficient amount to reduce the pH of the lotion composition (e.g. pH of less than about 5) may be useful as the preservative, or as a preservative enhancing agent for other preservative ingredients.

The cleansing composition also includes a carrier such as water. The cleansing composition may comprise greater than about 50%, greater than about 60%, greater than about 70%, greater than about 80%, greater than about 90%, greater than about 95%, greater than about 96%, or greater than about 97% by weight of water. The cleansing composition may have a pH in the range of about 3 to about 5, or about 3 to about 4, or about 3.5 to about 4, or less than 4. In addition, the cleansing composition may include various optional ingredients, such as surfactants, emollients, film-formers, preservatives, pH buffers, rheology modifiers, and the like, such as described in U.S. Pat. Nos. 7,666,827; 7,005,557; 8,221,774; and U.S. Patent Application Publication No. 2011/0268777. For example, the cleansing composition may comprise optional ingredients such as perfumes, aloe, and chamomile.

Preservative Enhancing Agent

The preservative system may include one or more preservative enhancing agents. Exemplary preservative enhancing agents include caprylyl glycol; caprylyl glyceryl ether; glyceryl caprylate; sorbitan caprylate; ethylhexyl glycerin, and the like. Such exemplary preservative enhancing agents are believed to be dermatologically safe. The safety profile of a cleansing composition for a wet wipe is important because the wet wipes may be used on the skin of babies, including pre-term and full-term newborns. An exemplary sorbitan caprylate is manufactured by Clariant under the designation VELSAN® SC. An exemplary ethylhexyl glycerin is manufactured by Schulke & Mayr GmbH of Germany under the designation SENSIVA® SC 50.

The cleansing composition may comprise from about 0.01% by weight to about 5.0% by weight of a preservative enhancing agent. The cleansing composition may comprise a single glucomannan, or the cleansing composition may comprise a combination of different glucomannans.

Additional preservative enhancing compounds may include chelators, such as ethylenediamine tetraacetic acid (EDTA) and its salts.

In some exemplary configurations, acidic compounds used in sufficient amount to reduce the pH of the cleansing composition (e.g. pH of less than about 5) may be useful as a preservative enhancing agent for the preservative system. Low pH buffering systems, such as a citrate-citric acid buffering system, such as trisodium citrate and citric acid, a pH of less than about 5, or less than about 4, may be employed as part of the preservative system.

Preservative

As previously mentioned, the preservative system of the cleansing composition may comprise one or more preservative enhancing agents and one or more preservatives. It has been found that a wet wipe having a cleansing composition comprising a preservative enhancing agent and a preservative has an improved antimicrobial performance compared to a wet wipe having a cleansing composition comprising a preservative without a preservative enhancing agent. As a result, lower concentrations of a preservative may be used in a cleansing composition comprising a preservative enhancing agent than may be used when the cleansing composition comprises a preservative without a preservative enhancing agent.

The cleansing composition may include one or more preservatives. The preservative may include an organic acid or the salt thereof. Exemplary organic acids include benzoic acid; lactic acid;

sorbic acid; malic acid; maleic acid; and the like. Exemplary salts of organic acids include sodium benzoate, for example.

The cleansing composition may comprise from about 0.1% by weight to about 5.0% by weight, or from about 0.12% by weight to about 1.0% by weight, of one or more preservative enhancing agents. The ratio of preservative to preservative enhancing agent present in the cleansing composition may be from about 1:0.5 to about 1:5, or from about 1:0.75 to about 1:3.125.

An exemplary wet wipe may include a cleansing composition comprising a preservative and a preservative enhancing agent. In an exemplary configuration, the cleansing composition may comprise sorbitan caprylate and benzoic acid. In another exemplary configuration, the cleansing composition may comprise caprylyl glycol and priroctone olamine.

The cleansing composition comprising a preservative and one or more preservative enhancing agents may be incorporated into a substrate at a load of about 200% to about 600% by weight of the substrate. A substrate comprising a relatively high amount of synthetic fibers may have a cleansing composition load of about 300% to about 600% by weight of the substrate.

Optional Cleansing Composition Ingredients

Additional ingredients may be added to the cleansing composition. The cleansing composition may generally comprise any of the following ingredients: emollients, surfactants, rheology modifiers, or other adjunct ingredients such as texturizers, colorants, soothing agents and medically active ingredients, such as healing actives and skin protectants. It is to be noted that some ingredient compounds can have a multiple function and that all compounds are not necessarily present in the cleansing composition. The cleansing composition may be an aqueous-based solution.

Emollient

The lotion composition may include an emollient. Emollients may (1) hydrate the residues (for example, fecal residues or dried urine residues or menses), thus enhancing their removal from the skin, (2) hydrate the skin, thus reducing its dryness and irritation while improving its flexibility under the wiping movement, (3) reduce the adhesive interaction between the soil and the surface, and (4) protect the skin from later irritation (for example, caused by the friction of an absorbent article) as the emollient is deposited onto the skin and remains at its surface as a thin protective layer.

An emollient may include silicone oils, functionalized silicone oils, hydrocarbon oils, fatty alcohols, fatty alcohol ethers, fatty acids, esters of monobasic and/or dibasic and/or tribasic and/or polybasic carboxylic acids with mono and polyhydric alcohols, polyoxyethylenes, polyoxypropylenes, mixtures of polyoxyethylene and polyoxypropylene ethers of fatty alcohols, and mixtures thereof. The emollients may be either saturated or unsaturated, have an aliphatic character and be straight or branched chained or contain alicyclic or aromatic rings.

In some exemplary configurations, the lotion composition may comprise a mixture of caprylic/capric triglycerides in combination with Bis-PEG/PPG-16/16 PEG/PPG-16/16 dimethicone known as ABIL® CARE 85, available from Degussa Care Specialties of Hopewell, Va.

Various emollients may function as emollients, while also providing skin benefits, including improving or maintain the integrity of the skin. For example, the lotion composition may comprise an omega-6 fatty acid. The lotion composition may comprise at least about 0.003%, from about 0.003% to about 35%, from about 0.015% to about 25%, or from about 0.06% to about 20%, by weight of the lotion and/or coating composition, of omega-6 fatty acid. Exemplary lotion compositions comprising omega-6 fatty acids are described in U.S. Patent Publication No. 2011/0159074 A1.

The omega-6 fatty acid may be added to the lotion composition as an emollient, such as from a vegetable oil. Therefore, in one exemplary configuration, the lotion composition comprises an emollient comprising omega-6 fatty acid. The lotion composition may comprise from about 0.1% to about 70%, from about 0.5% to about 50%, or from about 2% to about 40%, by weight of the lotion and/or coating composition, of the emollient. The emollient may comprise at least 3%, from about 3% to about 50%, or from about 5% to about 40%, by weight of the emollient, of omega-6 fatty acid.

Non-limiting examples of suitable emollients include high oleic canola Oil (Brassica campestris, B. napus, B. rapa; characterized by having an oleic fatty acid content greater than 70%, e.g., high oleic canola oil, very high oleic canola oil, or partially hydrogenated canola oil), manila kernel oil (Sclerocarya birrea), palm oil (Elaeis Guineensis Oil), palm olein, palm stearin, palm superolein, pecan oil, pumpkin seed oil, oleic safflower oil (Carthamus Tinctorius; characterized by having an oleic fatty acid content of greater than about 30% and omega-6 fatty acid content of less than about 50%, e.g., high oleic safflower oil), sesame oil (Sesamum indicum, S. oreintale), soybean oil (Glycine max, e.g., high oleic soybean, low linolenic soybean oil, partially hydrogenated), high oleic sunflower oil (Helianthus annus; characterized by having an oleic content of greater than about 40%, e.g., mid oleic sunflower or high oleic sunflower oil), and mixtures thereof. Oleic canola oil, palm oil, sesame oil, high oleic safflower oil, high oleic soybean oil, mid oleic sunflower oil, and high oleic sunflower oil are common plant-bred derived oils and may be also be derived from non-genetically modified organisms (non-GMO).

Non-limiting examples of emollients are commercially-available from a number of vendors, including Cargill for partially hydrogenated soybean oil (i.e., Preference® 110W Soybean Oil or Preference® 300 Hi Stability Soybean Oil), mid oleic sunflower oil (i.e., NuSun® Mid-Oleic Sunflower Oil), high oleic sunflower oil (i.e., Clear Valley® High Oleic Sunflower Oil), high oleic canola oil, very high oleic canola, and partially hydrogenated low erucic rapeseed oil (i.e., Clear Valley® 65 High Oleic Canola Oil and Clear Valley® 75 High Oleic Canola Oil); Lambert Technology for high oleic canola oil (i.e., Oleocal C104); Arch Personal Care for manila kernel oil; Pioneer for high oleic soybean oil (i.e., Plenish®); Asoyia for low linolenic soybean oil (i.e., Ultra Low Linolenic Soybean Oil®); and Dipasa, Inc. for refined sesame oil.

The emollient can further comprise a blend of oils, including those described supra, as well as additional emollients. Suitable additional emollients can include acai berry oil, almond oil, avocado oil, beech oil, brazil nut oil, camelina sativa oil (family Brassicaceae, e.g. Camelina Sativa, Gold of Pleasure, False Flax, etc.), camellia seed oil, canola oil, carrot seed oil, cashew nut oil, castor oil, cherry kernel oil, chia oil, corn oil, cottonseed oil, hydrogenated cottonseed oil, evening primrose oil, filbert (hazelnut) oil, grapeseed oil, hemp oil, hickory nut oil, jojoba oil, kukui oil, lanolin, olive oil (Olea europaea), macadamia oil, maringa oil, meadowfoam oil, neem oil, palm kernel oil, olive oil, passionflower oil (family Passiflora, Passiflora Incarnata), peanut oil, peach kernel oil, pistachio nut oil, rapeseed oil, rice bran oil, rose hip oil, safflower oil, sorghum oil, soybean oil, sunflower seed oil, tall oil, vegetable oil, vegetable squalene, walnut oil, wheat germ oil, and mixtures thereof. The emollient of the present invention can be selected from the group consisting of camelina sativa seed oil, oleic canola oil, evening primrose oil, manila kernel oil, palm oil, palm olein, palm stearin, palm superolein, Passiflora Incarnata seed oil, pecan oil, pumpkin seed oil, oleic safflower oil, sesame oil, soybean oil, oleic sunflower oil, vegetable oil, and mixtures thereof.

Suitable, commercially available emollients include a mixture of vegetable oil and camelina sativa seed oil (commercially-available as Lipex® Omega 3/6 from Aarhus Karlshamn Sweden AB), a mixture of vegetable oil and Passiflora Incarnata seed oil (commercially-available as Lipex® Omega Passiflora from Aarhus Karlshamn Sweden AB), a mixture of vegetable oil and evening primrose oil (commercially-available as Lipex Omega EPO from Aarhus Karlshamn Sweden AB), high oleic canola oil (commercially-available as Clear Valley® 75 High Oleic Canola Oil from Cargill), and mixtures thereof.

Surfactant

The lotion composition may include one or more surfactants. The surfactant can be an individual surfactant or a mixture of surfactants. The surfactant may be a polymeric surfactant or a non-polymeric one. The surfactant may be employed as an emulsifier. The surfactant may aid in dissolution and removal of the soils from the surface being cleansed. The surfactant or combinations of surfactants may be mild, which means that the surfactants provide sufficient cleaning or detersive benefits but do not overly dry or otherwise harm or damage the skin. The surfactant, when present in the lotion composition, may be present in an amount ranging from about 0.5%, 1%, or 4% by weight to about 0.001%, 0.01% or 0.02% by weight of the lotion composition. The surfactant may comprise PEG-40 Hydrogenated Castor Oil, manufactured by Clariant International Ltd. of Switzerland under the designation EMULSOGEN® HCW049.

A wide variety of surfactants are useful herein and include those selected from the group consisting of anionic surfactants, nonionic surfactants, cationic surfactants, amphoteric surfactants, zwitterionic surfactants, and mixtures thereof.

A wide variety of anionic surfactants are useful herein. Non-limiting examples of anionic surfactants include those selected from the group consisting of carboxylates, sarcosinates, sulfates, sulfonates, isethionates, taurates, phosphates, lactylates, glutamates, and mixtures thereof.

Nonionic surfactants useful herein include, but are not limited to, those selected from the group consisting of alkyl glucosides, alkyl polyglucosides, polyhydroxy fatty acid amides, alkoxylated fatty acid esters, alkoxylated fatty alcohol ethers, sucrose esters, and mixtures thereof.

Amphoteric surfactants suitable for use in the present compositions include those surfactants broadly described as derivatives of aliphatic secondary and tertiary amines in which the aliphatic radical can be straight or branched chain and wherein one of the aliphatic substituents contains from about 8 to about 18 carbon atoms and one contains an anionic water solubilizing group such as carboxy, sulfonate, sulfate, phosphate, or phosphonate. Useful amphoteric surfactants include the group consisting of cocoamphoacetate, cocoamphodiacetate, lauroamphoacetate, lauroamphodiacetate, and mixtures thereof.

Zwitterionic surfactants suitable for use herein include those surfactants broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group such as carboxy, sulfonate, sulfate, phosphate or phosphonate. Useful zwitterionic surfactants include betaines, amphoacetates and sulfobetaines, e.g., cocoamidopropylbetaine, sodium laurylamphoacetate and cocoamidopropylhydroxysultaine.

Rheology Modifier

The cleaning composition may comprise one or more rheology modifiers. A rheology modifier may (1) help to stabilize the lotion composition on a substrate, (2) enhance the transfer of the lotion composition to the skin, and (3) enhance the uniformity of the layer of the lotion composition on the skin. For example, rheology modifiers may help to preserve a homogeneous distribution of the lotion composition within a stack of the substrates. Any composition that is in fluid form may have a tendency to migrate to the lower part of the wipes stack during prolonged storage. This effect may create an upper part of the stack of substrates having less lotion composition than the bottom part of the stack.

Non-limiting examples of rheology modifiers include, but are not limited to, rheology modifiers comprising: polysaccharide units, e.g. cellulose, xanthan gum, diutan gum, carrageenan, gellan gum, welan gum, pectin, sclerotium gum, starch, galactoarabinan, alginate, and modified-forms thereof; homopolymers of acrylic acid; acrylic acid crosslinked with a polyfunctional compound, e.g. carbomer and acrylate crosspolymer; copolymers of acrylic acid, acrylate esters, maleic acid and the like, generally known as the alkali swellable emulsions (ASE) group; hydrophobically-modified copolymers of acrylic acid, acrylate esters, maleic acid and the like, generally known as the hydrophobically-modified alkali swellable emulsions (HASE) group; polyethylene glycol units of varying length connected by urethane linkages and terminated with hydrophobic end groups, generally known as the hydrophobically-modified ethoxylated urethane resins (HEUR) group; organoclays; silicas; and combinations thereof.

Rheology modifiers, when present in the lotion composition, may be present in the range of about 0.01%, 0.015%, or 0.02% by weight to about 2% by weight of the lotion composition.

EXAMPLE 1

Example 1 is an illustrative, non-limiting formula for a cleansing composition comprising a preservative enhancing agent and a preservative.

| Example 1 | |
|---|---|
| Ingredient Name | Weight % |
| Water | Q. S. |
| Disodium EDTA | 0.100 |
| Sodium Benzoate | 0.120 |
| Trisodium Citrate | 0.330 |
| Xanthan Gum | 0.180 |
| Aloe Barbadensis Leaf Extract[†] - Optional | 0.003 |
| Peg-40 Hydrogenated Castor Oil[□] | 0.440 |

-continued

| Example 1 | |
|---|---|
| Ingredient Name | Weight % |
| BIS-PEG/PPG-16/16 PEG/PPG-16/16 Dimethicone Caprylic Capric Triglyceride△ | 0.100 |
| Sorbitan Caprylate◇ | 0.1875 |
| Ethylhexylglycerine° | 0.030 |
| Perfume or Exaltolide - Optional | 0.05-0.08 |
| Bisabolol, Caprylic Capric Triglycerides, Chamomilla, Recutita Matricaria Flower Extract° - Optional | 0.003 |
| Citric Acid | 0.530 |
| Total | 100 |

†RITALOE ® 200M, available from R.I.T.A. Corporation of Crystal Lake, Illinois
□EMULSOGEN ® HCW 049, available from Clariant Corporation of Charlotte, NC
△ABIL ® Care 85, available from Evonik Industries of Germany ◇VELSAN ® SC, Clariant Corporation of Charlotte, NC
°SENSIVA ® SC 50 Schulke & Mayr GmbH of Germany
°Phytoconcentrol 2066530, available from Symrise AG of Holzminden, Germany Method of Making Cleansing Composition The method of making the cleansing composition of the present disclosure may include the following steps:

1. Dissolve salts, such as EDTA, sodium benzoate, and trisodium citrate) in water.
2. Add emulsifiers, such as PEG 40 hydrogenated castor oil; EMULSOGEN® HCW 049; and ABIL® Care 85, and/or rheology modifiers, such as xanthan gum, to Step 1.
3. Optionally add non-polar ingredient, such as aloe, to Step 2.
4. Add preservative enhancing agent, such as VELSAN® SC and ethylhyxyl glycerin, to Step 3.
5. Optionally add perfumes(s) to Step 4.
6. Optionally add ingredients such as aloe and chamomile, to Step 5.
7. Add pH lowering agent, such as citric acid, to Step 6.

Cleansing compositions such as Example 1 shown above may be prepared at a temperature in the range of 20-25° C. according to the following method.

1. Dispense the Q.S. of water and add disodium EDTA, sodium benzoate, and trisodium citrate and mix with an ULTRA-TURRAX® mixer (for example, model T-50 with a S 50 N-W 80 SMK Jet mixer head, available from IKA Works of Wilmington, N.C.).
2. Add xanthan gum and Ritaloe 200M to the dispersion of Step 1 and mix with the ULTRA-TURRAX® mixer at 5000-6000 rpm for 10 minutes.
3. Add EMULSOGEN® HCW 049 to the dispersion of Step 2 and mix with the ULTRA-TURRAX® mixer.
4. Add ABIL® Care 85 to the dispersion of Step 3 and mix with the ULTRA-TURRAX® mixer.
5. Add Sorbitan Caprylate, Ethylhexyl glycerin to the dispersion of Step 4 and mix with the ULTRA-TURRAX® mixer.
6. If adding Perfume add perfume to the dispersion in Step 5 and mix with the ULTRA-TURRAX® mixer.
7. Add phytoconcentrol 2066530 and citric acid to the dispersion of Step 6 and mix with the ULTRA-TURRAX® mixer.

The method of making the cleansing composition of Example 1 may occur in sequentially in the steps described above.

More particularly, cleansing compositions such as Example 1 shown above may be prepared at a temperature in the range of 20-25° C. according to the following method.

1. Dispense the Q. S. of water and add disodium EDTA, sodium benzoate, and trisodium citrate and mix with an ULTRA-TURRAX® mixer (for example, model T-50 with a S 50 N-W 80 SMK Jet mixer head, available from IKA Works of Wilmington, N.C.) at 5000-6000 rpm for 3 minutes.
2. Add xanthan gum and Ritaloe 200M to the dispersion of Step 1 and mix with the ULTRA-TURRAX® mixer at 5000-6000 rpm for 10 minutes.
3. Add EMULSOGEN® HCW 049 to the dispersion of Step 2 and mix with the ULTRA-TURRAX® mixer at 5000-6000 rpm for 3 minutes.
4. Add ABIL® Care 85 to the dispersion of Step 3 and mix with the UILTRA-TURRAX® mixer at 5000-6000 rpm for 3 minutes.
5. Add Sorbitan Caprylate, Ethylhexyl glycerin to the dispersion of Step 4 and mix with the ULTRA-TURRAX® mixer at 5000-6000 rpm for 3 minutes.
6. If adding Perfume add perfume to the dispersion in Step 5 and mix with the ULTRA-TURRAX® mixer at 5000-6000 rpm for 3 minutes.
7. Add phytoconcentrol 2066530 and citric acid to the dispersion of Step 6 and mix with the ULTRA-TURRAX® mixer at 5000-6000 rpm for 10 minutes.

The method of making the cleansing composition of Example 1 may occur in sequentially in the steps described above.

Substrate

A cleansing composition of the present disclosure may be loaded onto a substrate to form a wet wipe. The substrate may be a nonwoven material. The nonwoven material may comprise one or more layers of such fibrous assemblies, wherein each layer may include continuous fibers, coextruded fibers, non-continuous fibers and combinations thereof.

The fibers of the substrate may be comprised of any natural, cellulosic, and/or wholly synthetic material. Examples of natural fibers may include cellulosic natural fibers, such as fibers from hardwood sources, softwood sources, or other non-wood plants. The natural fibers may comprise cellulose, starch and combinations thereof. Non-limiting examples of suitable cellulosic natural fibers include wood pulp, typical northern softwood Kraft, typical southern softwood Kraft, typical CTMP, typical deinked, corn pulp, acacia, eucalyptus, aspen, reed pulp, birch, maple, radiata pine and combinations thereof. Other sources of natural fibers from plants include albardine, esparto, wheat, rice, corn, sugar cane, papyrus, jute, reed, sabia, raphia, bamboo, sidal, kenaf, abaca, sunn, rayon (also known as viscose), lyocell, cotton, hemp, flax, ramie and combinations thereof. Yet other natural fibers may include fibers from other natural non-plant sources, such as, down, feathers, silk, cotton and combinations thereof. The natural fibers may be treated or otherwise modified mechanically or chemically to provide desired characteristics or may be in a form that is generally similar to the form in which they can be found in nature. Mechanical and/or chemical manipulation of natural fibers does not exclude them from what are considered natural fibers with respect to the development described herein.

The synthetic fibers can be any material, such as those selected from the group consisting of polyesters (e.g., polyethylene terephthalate), polyolefins, polypropylenes, polyethylenes, polyethers, polyamides, polyesteramides, polyvinylalcohols, polyhydroxyalkanoates, polysaccharides, and combinations thereof. Further, the synthetic fibers can be a single component (i.e., single synthetic material or mixture makes up entire fiber), bi-component (i.e., the fiber is divided into regions, the regions including two or more different synthetic materials or mixtures thereof and may include co-extruded fibers and core and sheath fibers) and combinations thereof. Bicomponent fibers can be used as a component fiber of the structure, and/or they may be present to act as a binder for the other fibers present in the fibrous structure. Any or all of the synthetic fibers may be treated before, during, or after manufacture to change any desired properties of the fibers. The substrate may comprise hydrophilic fibers, hydrophobic fibers, or a combination thereof.

The substrate may comprise various percentages of natural and/or synthetic fibers. For example, in some exemplary configurations, the substrate may comprise 100% synthetic fibers. In another exemplary configuration, the substrate may comprise natural and synthetic fibers. For example, the substrate may comprise from about 0% to about 90% natural fibers, with the balance comprising synthetic fibers. The substrate may be comprised of 10%, 20%, 30%, 40%, 50%, 60%, 70%, or 80% natural fibers.

In certain configurations, it may be desirable to have particular combinations of fibers to provide desired characteristics. For example, it may be desirable to have fibers of certain lengths, widths, coarseness or other characteristics combined in certain layers, or separate from each other.

The fibers may be of virtually any size and may have an average length from about 1 mm to about 60 mm. Average fiber length refers to the length of the individual fibers if straightened out. The fibers may have an average fiber width of greater than about 5 micrometers. The fibers may have an average fiber width of from about 5 micrometers to about 50 micrometers. The fibers may have a coarseness of greater than about 5 mg/100 m. The fibers may have a coarseness of from about 5 mg/100 m to about 75 mg/100 m.

The fibers may be circular in cross-section, dog-bone shape, delta (i.e., triangular cross section), trilobal, ribbon, or other shapes typically produced as staple fibers. Likewise, the fibers can be conjugate fibers such as bicomponent fibers. The fibers may be crimped and may have a finish, such as a lubricant, applied.

The substrate materials may also be treated to improve the softness and texture thereof. The substrate may be subjected to various treatments, such as physical treatment, hydromolding, hydro-embossing, and ring rolling, as described in U.S. Pat. No. 5,143,679; structural elongation, as described in U.S. Pat. No. 5,518,801; consolidation, as described in U.S. Pat. Nos. 5,914,084; 6,114,263; 6,129,801 and 6,383, 431; stretch aperturing, as described in U.S. Pat. Nos. 5,628,097; 5,658,639; and 5,916,661; differential elongation, as described in U.S. Pat. No. 7,037,569, and other solid state formation technologies as described in U.S. Pat. Nos. 7,553,532 and 7,410,683; zone activation, and the like; chemical treatment, such as rendering part or all of the substrate hydrophobic, and/or hydrophilic, and the like; thermal treatment, such as thermal-embossing, softening of fibers by heating, thermal bonding and the like; and combinations thereof.

Without wishing to be bound by theory, it is believed that a textured substrate may further enable the ease of removal of soils by improving the ability to grip or otherwise lift the soils from the surface during cleansing. Any one of a number of texture elements may be useful in improving the ability to grip or otherwise lift the soil from the surface during cleansing such as continuous hydro-molded elements, hollow molded element, solid molded elements, circles, squares, rectangles, ovals, ellipses, irregular circles, swirls, curly cues, cross hatches, pebbles, lined circles, linked irregular circles, half circles, wavy lines, bubble lines, puzzles, leaves, outlined leaves, plates, connected circles, changing curves, dots, honeycombs, and the like, and combinations thereof. The texture elements may be hollow elements. The texture elements may be connected to each other. The texture elements may overlap each other.

The substrate may have a basis weight between about 15, 30, 40, or 45 grams/m$^2$ and about 65, 75, 85, 95, or 100 grams/m$^2$. A suitable substrate may be a carded nonwoven comprising a 40/60 blend of viscose fibers and polypropylene fibers having a basis weight of 58 grams/m$^2$ as available from Suominen of Tampere, Finland as FIBRELLA® 3160. FIBRELLA® 3160 is a 58 grams/m$^2$ nonwoven web comprising 60% by weight of 1.5 denier polypropylene fibers and 40% by weight of 1.5 denier viscose fibers. Another suitable material may be FIBRELLA® 3100 which is a 62 grams/m$^2$ nonwoven web comprising 50% by weight of 1.5 denier polypropylene fibers and 50% by weight of 1.5 denier viscose fibers. In both of these commercially available fibrous webs, the average fiber length is about 38 mm. Another suitable material for use as a substrate may be SAWATEX® 2642 as available from Sandler AG of Schwarzenbach/Salle, Germany. Yet another suitable material for use as a substrate may have a basis weight of from about 50 grams/m$^2$ to about 60 grams/m$^2$ and have a 20/80 blend of viscose fibers and polypropylene fibers. The substrate may also be a 60/40 blend of pulp and viscose fibers. Exemplary nonwoven substrates are described in U.S. Patent Publication 2012/066852 and U.S. Patent Publication U.S. 2011/244199.

In some configurations, the surface of the substrate may be essentially flat. In other configurations, the surface of the substrate may optionally contain raised and/or lowered portions. The raised and/or lowered portions can be in the form of logos, indicia, trademarks, geometric patterns, and/or images of the surfaces that the substrate is intended to clean (i.e., infant's body, face, etc.). The raised and/or lowered portions may be randomly arranged on the surface of the substrate or be in a repetitive pattern of some form.

In yet other configurations, the substrate may be biodegradable. For example, the substrate could be made from a biodegradable material such as a polyesteramide, or a high wet strength cellulose. In some exemplary configurations, the substrate may be dispersible.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A wet wipe comprising a cleansing composition and a substrate, wherein the cleansing composition comprises:
   a preservative enhancing agent comprising between about 0.01% and about 0.1875% sorbitan caprylate, by weight of the cleansing composition;
   a preservative, wherein the preservative comprises benzoic acid or a salt thereof; and
   a citrate-citric acid buffering system or citric acid;
   wherein the cleansing composition comprises at least 97.1% water, by weight of the cleansing composition;
   wherein the cleansing composition has a pH of less than 5; and
   wherein the preservative to the preservative enhancing agent weight ratio in the cleansing composition is from about 1:0.5 to about 1:5.

2. The wet wipe of claim 1, wherein the preservative enhancing agent further comprises: caprylyl glycol, caprylyl glyceryl ether, glyceryl caprylate, ethylhexyl glycerin, or combinations thereof.

3. The wet wipe of claim 1, wherein the preservative comprises benzoic acid.

4. The wet wipe of claim 1, wherein the preservative comprises sodium benzoate.

5. The wet wipe of claim 1, wherein the cleansing composition comprises aloe.

6. The wet wipe of claim 1, wherein the cleansing composition comprises a rheology modifier selected from the group of: cellulose, xanthan gum, diutan gum, carrageenan, gellan gum, welan gum, pectin, *sclerotium* gum, starch, galactoarabinan, alginate, and combinations thereof.

7. The wet wipe of claim 1, wherein the buffering system comprises trisodium citrate and citric acid.

8. The wet wipe of claim 1, wherein the cleansing composition comprises a surfactant.

9. The wet wipe of claim 8, wherein the surfactant comprises a non-ionic surfactant.

10. The wet wipe of claim 9, wherein the surfactant comprises PEG-40 hydrogenated castor oil.

11. A wet wipe comprising a cleansing composition and a substrate, wherein the cleansing composition comprises:
    between about 0.01% and about 0.1875% of a preservative enhancing agent by weight of the cleansing composition selected from the group of: caprylyl glycol, caprylyl glyceryl ether, glyceryl caprylate, ethylhexyl glycerin, sorbitan caprylate, and combinations thereof;
    a preservative, wherein the preservative comprises benzoic acid or a salt thereof; and
    a citrate-citric acid buffering system or citric acid;
    wherein the cleansing composition comprises at least 97.1% water, by weight of the cleansing composition;
    wherein the cleansing composition has a pH less than 5; and
    wherein the preservative to the preservative enhancing agent weight ratio in the cleansing composition is from about 1:0.5 to about 1:5.

12. The wet wipe of claim 11, wherein the preservative comprises benzoic acid.

13. The wet wipe of claim 11, wherein the preservative comprises sodium benzoate.

14. The wet wipe of claim 11, wherein the cleansing composition comprises aloe.

15. The wet wipe of claim 11, wherein the cleansing composition comprises a rheology modifier selected from the group of: cellulose, xanthan gum, diutan gum, carrageenan, gellan gum, welan gum, pectin, *sclerotium* gum, starch, galactoarabinan, alginate, and combinations thereof.

16. The wet wipe of claim 11, wherein the buffering system comprises trisodium citrate and citric acid.

17. The wet wipe of claim 11, wherein the cleansing composition comprises a surfactant.

18. The wet wipe of claim 17, wherein the surfactant comprises a non-ionic surfactant.

19. The wet wipe of claim 18, wherein the surfactant comprises PEG-40 hydrogenated castor oil.

20. A method of making a cleansing composition, the method comprising the steps of:
    dissolving benzoic acid and/or a salt thereof with water to form a solution;
    adding a rheology modifier to the solution;
    adding an emulsifier to the solution;
    adding sorbitan caprylate to the solution; and
    adding citric acid to the solution;
    wherein the cleansing composition comprises from about 0.01% to about 0.1875% of the sorbitan caprylate, by weight of the cleansing composition;
    wherein the cleansing composition comprises at least 97.1% water, by weight of the cleansing composition; and
    wherein the benzoic acid to sorbitan caprylate ratio in the cleansing composition is from about 1:0.5 to about 1:5, by weight of the cleansing composition.

* * * * *